United States Patent [19]

Yamanaka et al.

[11] Patent Number: 5,176,916
[45] Date of Patent: Jan. 5, 1993

[54] MEDICAL ADHESIVES

[75] Inventors: Akihito Yamanaka; Saburo Otsuka; Yoshifumi Hosaka, all of Ibaraki, Japan

[73] Assignees: Nitto Electric Industrial Co., Ltd.; Takeda Chemical Industries, Ltd., Osaka, Japan

[21] Appl. No.: 686,383

[22] Filed: Apr. 17, 1991

[30] Foreign Application Priority Data

Apr. 18, 1990 [JP] Japan .................. 2-104294

[51] Int. Cl.⁵ ............................. A61F 43/00
[52] U.S. Cl. ....................... 424/448; 424/449
[58] Field of Search ............ 421/447, 448, 449, 443

[56] References Cited

U.S. PATENT DOCUMENTS

| | | | |
|---|---|---|---|
| 4,455,146 | 6/1984 | Noda et al. | 424/448 |
| 4,732,808 | 3/1988 | Krampe et al. | 424/448 |
| 4,855,142 | 8/1989 | Fankhauser et al. | 424/434 |
| 4,913,905 | 4/1990 | Fankhauser et al. | 424/449 |
| 4,946,853 | 8/1990 | Bannon et al. | 424/449 |
| 4,983,396 | 1/1991 | Boder et al. | 424/449 |

FOREIGN PATENT DOCUMENTS

| | | |
|---|---|---|
| 0209975 | 1/1987 | European Pat. Off. |
| 0280737 | 9/1988 | European Pat. Off. |
| 0359004 | 3/1990 | European Pat. Off. |
| 02253 | 1/1985 | Japan |
| 24517 | 2/1986 | Japan |
| 221121 | 10/1986 | Japan |

Primary Examiner—Thurman K. Page
Assistant Examiner—Leon R. Horne
Attorney, Agent, or Firm—Sughrue, Mion, Zinn, Macpeak & Seas

[57] ABSTRACT

A medical adhesive comprising a plaster layer containing the following ingredients, characterized in that the ingredient ② is incorporated in a larger amount than the ingredient ⑤ and in an amount not less than 25% by weight relative to the total amount of the ingredients ①~⑤, and the plaster layer is a W/O type:
① a medicinal ingredient,
② a hydrophobic polymer having a glass transition temperature (Tg) of −65° C. to 35° C.
③ a percutaneous absorption-promoting agent,
④ water, and
⑤ a hydrophilic polymer which is soluble or capable of swelling in water; and a medical adhesive which comprises a porous base layer in the plaster layer or in contact with the plaster layer, which enable stable release of the medicinal ingredient, the percutaneous absorption-promoting agents and so on and sustaining of the pharmacological effects over a long period.

14 Claims, 2 Drawing Sheets

← separate liner 4
← plaster layer 1
← porous base layer 3
← backing layer 2

MEDICAL ADHESIVES

BACKGROUND OF THE INVENTION

This invention relates to a medical adhesive which is excellent in terms of release and percutaneous and per mucosa (hereinafter when referred to as percutaneous, the term includes per mucosa unless otherwise specified) absorption of medicinal ingredients from a preparation. Ease of producibility and stability of the preparation are also maintained.

A wide variety of preparations have been developed as adhesives for topical applications. In recent years, percutaneous administration has drawn attention as an efficient administration route for of medicines, and some adhesives for systemic actions, for example, preparations of nitroglycerin, isosorbide dinitrate, scopolamine, clonidine and estradiol are marketed. Most of the medicinal ingredients of these marketed preparations are suitable for percutaneous absorption in view of their physical properties and levels of effective concentration in blood, and are relatively easily formed into preparations.

However, medicinal ingredients consisting of hydrophilic compounds in the form of salts or the like are generally difficult to absorb percutaneously, and even release of the medicinal ingredients from the preparations is often difficult in matrix type adhesives in which the medicinal ingredients are incorporated or dispersed in polymers having relatively high hydrophobicity which are in wide use as the bases for adhesives.

As one of the means for improving absorbability of medicinal ingredients in such cases release from the preparations or percutaneous absorbability of the medicinal ingredients may be enhanced by increasing the fat-solubility of the medicinal ingredients themselves. For example, the medicinal ingredients may be used which have been in advance converted into their free bases in the base of the preparation; or free bases of the medicinal ingredients may be formed in the preparation.

As another means of improvement, incorporation of percutaneous absorption-promoting agents may be employed. Active studies have recently been made of absorption-promoting agents, and a number of absorption-promoting agents have been reported. Many examples of the adhesives containing absorption-promoting agents are described in, for example, unexamined Japanese Patent Application Nos. 24517/1986 and 221121/1986. However, the solubility of the medicinal ingredients in the base, release thereof from the base, or percutaneous absorbability of such adhesives are not satisfactory.

For the preparations in which the afore-mentioned medicinal ingredients having relatively high hydrophilicity are incorporated in bases mainly consisting of a hydrophobic polymer to exhibit solubility, release and percutaneous absorbability of the medicinal ingredients as expected, solubilizers for the medicinal ingredients are normally necessary. As a solubilizer for medicinal ingredients, water is generally selected in view of its low stimulus against the skin. As the examples of such adhesives in which water is used as a solubilizer, mention can be made of the adhesives as described in unexamined Japanese Patent Publication No. 02253/1985, wherein no absorption-promoting agent is contained, permitting relatively easy provision of stable plaster layers.

This invention relates to an improvement of the adhesives using water as a solubilizer as mentioned above.

The present invention provides a medical adhesive exhibiting excellent release and percutaneous absorption of the medicinal ingredient, which comprises a base mainly consisting of a hydrophobic polymer, an effective amount of a medicinal ingredient of low solubility in said hydrophobic polymer or poor in release from said hydrophobic polymer and an effective amount of percutaneous absorption-promoting agents which are admixed with or dispersed throughout said base. For the purpose of obtaining such an adhesive, a solubilizer for the medicinal ingredient is normally required.

The effective amounts of medicinal ingredients are generally determined primarily on the basis of the results of initial studies of physical properties, pharmacological effects, effective concentration in blood and the like of the medicinal ingredients, and the effective amounts are not in general determined taking account of the forms and usability of the preparations. This results in a problem that a stable preparation which exhibits the expected pharmacological effect cannot be necessarily obtained in many cases only by incorporating and mixing an effective amount of said medicinal ingredients, an effective amount of percutaneous absorption-promoting agents and the other ingredients.

In the present invention, for example, at least one percutaneous absorption-promoting agent is used. Percutaneous absorption-promoting agents are generally classified into two types, hydrophobic absorption-promoting agents and hydrophilic absorption-promoting agents as mentioned below, and they are normally used solely or in combination. In some cases, poor compatibility of the percutaneous absorption-promoting agents with solubilizers for medicinal ingredients or hydrophobic polymers, gives rise to separation of the ingredients during the course of production of the preparations or with the lapse of days after production, which results in failure to provide the desired adhesives.

Below, examples of the combination where compatibility is poor are given, including the above case.
a) a hydrophobic absorption-promoting agent and a hydrophilic absorption-promoting agent;
b) a hydrophobic absorption-promoting agent and a solubilizer for medicinal ingredients;
c) a hydrophobic polymer or a solution thereof in an organic solvent and a hydrophilic absorption-promoting agent; and
d) a hydrophobic polymer or a solution thereof in an organic solvent and a solubilizer for medicinal ingredients.

As mentioned above, compatibility of each component is critical to feasibility of the preparations for those containing multiple components, and when components of the preparation have poor compatibility, the preparation lacks stability.

SUMMARY OF THE INVENTION

An object of the present invention is to provide an adhesive comprising a base mainly composed of a hydrophobic polymer, in which a medicinal ingredient which is difficult to absorb percutaneously; for example, a medicinal ingredient having relatively high hydrophilicity, is incorporated and water as a solubilizer is further contained, and having satisfactory solubility, release properties and percutaneous absorption of the medicinal ingredients.

Another object of the present invention is to provide an adhesive as mentioned above which exhibits excellent stability as a preparation and is easily produced.

The inventors of the present invention have made intensive studies for the purpose of solving the beforementioned problems, and as a result, obtained the following findings.

Water used as a solubilizer is inferior in compatibility with a hydrophobic polymer, and use of a large amount of water makes uniform mixture difficult. The present inventors have found that the steps of (1) incorporating a hydrophilic polymer which is soluble or capable of swelling in water for increasing viscosity of a solution and (2) mixing the solution with a solution of a hydrophobic polymer in an organic solvent, followed by homogeneous dispersion suppress separation among the respective components in the obtained applicable solution or the plaster layer obtained by drying same, even if a large amount of water is incorporated, and sufficient solubility, release and percutaneous absorbability of the medicinal ingredients can be attained. Moreover, the inventors have found that a preparation of particularly stable systems can be obtained by incorporating the hydrophobic polymer as the main component of the base in a proportion of not less than 25% by weight relative to the total amount of the below-mentioned ingredients ①~⑤ excluding the organic solvent of the hydrophobic polymer and further making the plaster layer of the finished adhesive a W/O type.

The present invention has been completed on the basis of the foregoing findings and is summarized as follows:

(1) A medical adhesive comprising a plaster layer containing the following ingredients, characterized in that the ingredient ② is incorporated in a larger amount than the ingredient ⑤ and in an amount not less than 25% by weight relative to the total amount of the ingredients ①~⑤, and the plaster layer is a W/O type:
① a medicinal ingredient,
② a hydrophobic polymer having a glass transition temperature (Tg) of −65° C. to 35° C.,
③ a percutaneous absorption-promoting agent,
④ water, and
⑤ a hydrophilic polymer which is soluble or capable of swelling in water; and (2) a medical adhesive as described in (1), which comprises a porous base layer in the plaster layer or in contact with the plaster layer.

In the adhesive according to the present invention, water is incorporated as a solubilizer in an amount necessary for making the plaster layer a W/O type.

DETAILED DESCRIPTION OF THE INVENTION

As percutaneously absorbable preparations containing water, for example, ointments, cream preparations, lotions, liquid preparations, suspensions, emulsions may be used, besides adhesives. These preparations can be classified into solution types, dispersion types such as W/O (water in oil) type or O/W (oil in water) type, and other types. To obtain an adhesive to satisfy the objects of the present invention in that the adhesive contains water, has high shape-retention property and excellent stability during the storage thereof and remains stable during the period from administration to removal thereof, it is required that a hydrophobic polymer, which is a continuous phase, namely a W/O type, is selected for the base.

Hereinbelow, the invention is described in detail.

There is no limitation on the medicinal ingredient (ingredient①) to be used for the present invention as long as it can display the expected actions through percutaneous administration. Especially desirable are the drugs 1 g of or 1 ml of which can be dissolved in an amount of less than 10,000 ml, particularly less than 1,000 ml (most preferably less than 100 ml) of water. Such drugs which come to have the above-mentioned solubility in water as a result of concomitance with an acid or a base are also useful in the present invention. The medicinal ingredients preferably have a molecular weight of 50–1,000, more preferably 100–500.

More specific examples of such drugs are as follows:
[1] general anesthetics
barbiturate: thiamylal sodium, thiopental sodium, pentobarbital sodium, etc.;
other miscellanea: ketamine hydrochloride, etc.
[2] hypnotics and sedatives
benzodiazepine drugs: flurazepam hydrochloride, etc.;
barbiturate drugs: amobarbital sodium, phenobarbital, pentobarbital calcium, etc.;
other miscellanea: bromovalerylurea, chloral hydrate, etc.;
[3] antiepileptics
hydantoin drugs: phenytoin sodium, ethotoin, etc.;
barbiturate drugs: phenobarbital sodium, etc.;
other miscellanea: trimethadione, primidone, ethosuximide, carbamazepine, sodium valproate, etc.;
[4] antipyretics, analgesics and antiinflammatory agents
aniline derivative drugs: acetaminophen, phenacetin, etc.;
salicylic acid drugs: aspirin, sodium salicylate, etc.;
pyrazolone drugs: aminopyrine, antipyrine, sulpyrine, etc.;
basic inflammatory drugs: mepirizole, tiaramide hydrochloride, perixazole citrate, etc.;
other miscellanea: diclofenac sodium, anfenac sodium, buprenorphine hydrochloride, butorphanol tartrate, eptazocine hydrobromide, etc.;
[5] agents for dizziness
dimenhydrinate, difenidol hydrochloride, dl-isoprenaline hydrochloride, etc.;
[6] psychotropic drugs
phenothiazine drugs: chlorpromazine hydrochloride, levomepromazine maleate, thioridazine hydrochloride, fluphenazine hydrochloride, etc.;
drugs of phenothiazine-like structures: thiothixene, flupenthixol hydrochloride, etc.;
butyrophenone drugs: floropipamide hydrochloride, moperone hydrochloride, etc.;
carpipramine drugs: carpipramine hydrochloride, clocapramine hydrochloride, etc.;
tricyclic antidepressants: imipramine hydrochloride, desipramine hydrochloride, etc.;
tetracyclic antidepressants: mianserin hydrochloride, maprotiline hydrochloride, etc.;

benzodiazepine drugs: chlordiazepoxide hydrochloride, dipotassium clorazepate, etc.;
other miscellanea: meprobamate, hydroxyzine hydrochloride, saflazine hydrochloride, etc.;

[7] local anesthetics
aminobenzoic acid alkamine ester drugs: tetracaine hydrochloride, procaine hydrochloride, etc.;
other miscellanea: ethyl aminobenzoate, dibucaine hydrochloride, lidocaine hydrochloride, etc.;

[8] skeletal muscle relaxants
carbamate drugs: chlorphenesin carbamate, methocarbamol, etc.;
alkaloid drugs: alcuronium chloride, tubocurarine chloride, etc.;
other miscellanea: suxamethonium chloride, eperisone hydrochloride, etc.;

[9] autonomic nerve drugs
cholinergic drugs: acetylcholine chloride, etc.;
cholinesterase inhibitor: neostigmine bromide, etc.;

[10] antispasmodics
choline blocker: atropine sulfate, scopolamine hydrobromide, etc.;
other miscellanea: papaverine hydrochloride, etc.;

[11] drugs for Parkinson's desease
biperiden hydrochloride, trihexyphenidyl hydrochloride, amantadine hydrochloride, piroheptine hydrochloride, profenamine hydrochloride, levodopa, mazaticol hydrochloride, etc.;

[12] antihistaminics
ethanolamine compounds: diphenhydramine hydrochloride, carbinoxamine maleate, etc.;
monoamine compounds: dl-chlorpheniramine maleate, etc.; phenothiazine compounds: promethazine, alimemazine tartrate, etc.;
other miscellanea: isothipendyl hydrochloride, clemizole hydrochloride, cyproheptadine hydrochloride, clemastine fumarate, etc.;

[13] cardiacs
xanthine derivatives: aminophylline, choline theophylline, caffeine and sodium benzoate, etc.;
sympathomimetic agents: dl-isoproterenol hydrochloride, dopamine hydrochloride, dobutamine hydrochloride, etc.; other miscellanea: methyldigoxin, etc.;

[14] antiarrhythmics
$\beta$-blockers: propranolol hydrochloride, alprenolol hydrochloride, bupranolol hydrochloride, timolol maleate, metoprolol tartrate, etc.;
other miscellanea: procainamide hydrochloride, lidocaine hydrochloride, quinidine sulfate, ajmaline, verapamil hydrochloride, aprindine hydrochloride, etc.;

[15] diuretics
thiazide drugs: ethiazide, hydrochlorothiazide, etc.;
other miscellanea: acetazolamide, isosorbide, etacrynic acid, etc.;

[16] antihypertensives
ACE inhibitor drugs: captopril, enalapril maleate, delapril hydrochloride, alacepril, (R)-3-[(S)-1-carboxy-5-(4-piperidyl) pentyl]amino-4-oxo-2,3,4,5-tetrahydro-1,5-benzothiazepine-5-acetic acid, etc.;
hydralazine drugs: ecarazine hydrochloride, hydralazine hydrochloride, etc.;
other miscellanea: hexamethonium bromide, clonidine hydrochloride, bunitrolol hydrochloride, propranolol hydrochloride, methyldopa, guanethidine sulfate, bethanidine sulfate, etc.;

[17] vasoconstrictors
phenylephrine hydrochloride, methoxamine hydrochloride, etc.;

[18] coronary vasodilators
diltiazem hydrochloride, varapamil hydrochloride, isosorbide dinitrate, nicorandil, etc.;

[19] peripheral vasodilators
nicametate citrate, nicotinic-alcohol tartrate, tolazoline hydrochloride, etc.;

[20] drugs for arteriosderosis
simfibrate, etc.;

[21] other drugs for circulatory organs
nicardipine hydrochloride, ifenprodil tartrate, piperidinocarbamate, cinepazide maleate, thiapride hydrochloride, etc.;

[22] respiratory agents
dimorpholamine drugs: dimorpholamine, levallorphan tartrate, etc.;
other miscellanea: lobeline hydrochloride, naloxone hydrochloride, etc.;

[23] antitussives, expectorants
central antitussives: codeine phosphate, dextromethorphan hydrobromide, etc.;
other antitussives: noscapine hydrochloride, etc.; expectorants: bromhexine hydrochloride, ambroxol hydrochloride, etc.;
xanthine derivatives: theophylline, diprophylline, etc.; sympathetic nerve-stimulants: dl-epinephrine hydrochloride ephedrine hydrochloride, isoproterenol sulfate, salbutamol tulobuterol hydrochloride, etc.;
anti-allergic drugs: ketotifen fumarate, azelastine hydrochloride, etc.;
other miscellanea: ipratropium bromide, etc.;

[24] hormone drugs hydrocortisone, dexamethasone sodium phosphate, prednisolone, norethisterone, clomiphene citrate, etc.;

[25] external drugs for suppurative diseases
sulfa drugs: mafenide acetate, sulfamethoxazole sodium, etc.; antibiotics: tetracycline hydrochloride, etc.;

[26] analagenic, antipruritic, astringent antiinflammatory drugs methyl salicylate, isothipendyl hydrochloride, diphenhydramine, prednisolone, ethyl aminobenzoate, crotamiton, etc.;

[27] drugs for parasitic dermal diseases
salicylic acid, nystatin, econazole nitrate, cloconazole hydrochloride, etc.;

[28] vitamins
vitamin $B_1$: thiamine hydrochloride, cycothiamine hydrochloride, etc.;
vitamin $B_2$: riboflavin, riboflavin sodium phosphate, etc.;
vitamin $B_6$: pyridoxine hydrochloride, pyridoxal phosphate, pyridoxamine phosphate, etc.;
other miscellanea: nicotinic acid, nicotinamide, calcium pantothenate, pantothenol, panthetin, biotin, ascorbic acid, etc.;

[29] hemostatic drugs
tranexamic acid, ethamsylate, protamine sulfate, etc.;

[30] drugs for treatment of gout
colchicine, allopurinol

[31] antidiabetics
tolazamide, glymidine sodium, glybuzole, metoformin hydrochloride, buformin hydrochloride, etc.;

[32] miscellaneous metabolic drugs
orotic acid, azathioprine, lactulose, etc.;

[33] antineoplastic agents alkylating drugs: nitrogen mustard N-oxide hydrochloride, cyclophophamide, thio-TEPA, nimustine hydrochloride, etc.; antimetabolite drugs: thioinosine, fluorouracil, tegafur, etc.;

plant alkaloids: vinblastine sulfate, vincristine sulfate, vindesine sulfate, etc.;

carcinostatic antibiatics: mitomycin C, daunorubicin hydrochloride, aclarubicin hydrochloride, etc.;

other miscellanea: procarbazine hydrochloride, cisplatin, etc.;

[34] antibiotics natural penicillins: benzylpenicillin potassium, etc.;

semisynthetic penicillins: amoxicillin, amplicillin, etc.;

caphems: cefalexin, cefazolin sodium, etc.;

macrolides: erythromycin, kitasamycin tartrate, etc.;

chloramphenicols: chloramphenicol, thiamphenicol, etc.;

tetracycline types: tetracycline hydrochloride, minocycline hydrochloride, etc.;

lincomycins: lincomycin hydrochloride, clindamycin hydrochloride, etc.;

aminoglycosides: streptomycin sulfate, kanamycin sulfate, fradiomycin sulfate, gentamycin sulfate, etc.;

other miscellanea: spectinomycin hydrochloride, cycloserine, etc.;

[35] chemotherapeutic drugs sulfisomidine, isoniazid, ethambutol, acyclovin, etc.;

[36] narcotics analkaloid drugs: morphine hydrochloride, codeine phosphate, etc.;

cocaalkaloid drugs: cocaine hydrochloride, etc.;

synthetic narcotics: pethidine, fentanyl citrate, etc.;

While the amount of the medicinal ingredient to be incorporated in the present invention is not particularly limited provided that the medicinal ingredient displays the desired pharmacological effects, the preferred amount is in the range from 0.1 to 50% by weight relative to the weight of the plaster in which the medicinal ingredient is contained, more preferably from 1 to 30% by weight, and is in the range from 20 to 5,000 $\mu g/cm^2$ per unit area, preferably from 100 to 3,000 $\mu g/cm^2$.

The hydrophobic polymer (ingredient ②) to be used in the present invention is the main ingredient constituting the continuous phase of the W/O type plaster, which contains a medicinal ingredient, percutaneous absorption-promoting agents, water and a hydrophilic polymer. The hydrophobic polymer is not limited provided that it is capable of imparting the objective adhesives with adhesion to the skin and acting for shape-retention of the adhesives. It is extremely important not to lose shape-retention in view of the fact that it is difficult for the adhesives of the present invention containing water to retain shape.

It is necessary that the hydrophobic polymer is incorporated in an amount of not less than 25% by weight relative to the total amount of the ingredients ① ~ ⑤, preferably 25-80% by weight. Where the hydrophobic polymer is incorporated in an amount of less than 25% by weight, it fails to contain and to retain the other ingredients, especially percutaneous absorption-promoting agents which are in a liquid form at room temperature, and water stably, resulting in failure to maintain its shape-retention.

As the hydrophobic polymers, pressure-sensitive adhesive polymers exemplified by acrylic-type polymers; gum-type polymers such as silicone gums, polyisobutylene gums, polyisoprene gums and styrene-butadiene (or-isoprene)-styrene block copolymer gums; poly vinylalkyl ether-type polymers; vinyl-type polymers such as poly vinyl-acetate and poly vinyl-propionate; and polyurethane elastic bodies may be used in the present invention.

Among those, particularly preferred are pressure-sensitive adhesive acryl-type copolymers for adhesivity to the skin. Examples of preferred polymers include one polymer or two or more polymers of alkyl esters of (meth)acrylic acid such as butyl (meth)acrylate, pentyl (meth)acrylate, hexyl (meth)acrylate, heptyl (meth)acrylate, octyl (meth)acrylate, nonyl (meth)acrylate, decyl (meth)acrylate, undecyl (meth)acrylate, dodecyl (meth)acrylate and tridecyl (meth)acrylate, or copolymers of one or more species of said esters with a monomer copolymerizable therewith.

Examples of the copolymerizable monomers include functional monomers exemplified by carboxyl group-containing monomers such as (meth)acrylic acid, itaconic acid, crotonic acid, maleic acid, maleic anhydride and fumaric acid; sulfoxyl group-containing monomers such as styrenesulfonic acid, allylsulfonic acid, sulfopropylacrylate, (meth)acryloyloxynaphthalenesulfonic acid, acrylamidemethylpropanesulfonic acid and acryloxyloxybenzenesulfonic acid; hydroxyl group-containing monomers such as hydroxyethyl (meth)acrylate and hydroxypropyl (meth)acrylate; amido group-containing acrylic-type monomers such as (meth)acrylamide, dimethyl(meth)acrylamide, N-butylacrylamide, tetramethylbutylacrylate and N-methylol(-meth)acrylamide; alkylaminoalkyl group-containing acrylic-type monomers such as aminoethyl (meth)acrylate, dimethylaminoethyl (meth)acrylate, diethylaminoethyl (meth)acrylate and tert-butyl (meth)acrylate,; ether linkage-containing alkyl ester of acrylic acid such as methoxyethyl (meth)acrylate, ethoxyethyl (meth)acrylate, butoxyethyl (meth)acrylate, tetrahydrofurfuryl (meth)acrylate, methoxydiethylene glycol (meth)acrylate, methoxydiethylene glycol (meth)acrylate and methoxypolypropylene glycol (meth)acrylate; vinyl-type monomers such as N-(meth)acryloylamino acid and acrylic-type monomers such as urethane, urea and isocyanate esters of acrylic acid, and vinyl-type monomers exemplified by (meth)acrylonitrile, vinyl acetate, vinyl propionate, vinyl pyrrolidone, vinyl pyridine, vinyl pyrazine, vinyl piperazine, vinyl piperadone, vinyl pyrimidine, vinyl pyrrole, vinyl imidazole, vinyl caprolactam, vinyl oxazole, vinyl thiazole, vinyl morpholine, styrene, α-methylstyrene and bis[N,N'-dimethylaminoethyl]maleate.

The afore-mentioned alkyl esters of (meth)acrylic acid and copolymerizable monomers in the present invention include a variety of isomers in which the alkyl moiety is straight chain or branched chain, and various isomers which have substituents at different positions, and their derivatives.

The proportion of the above alkyl ester of (meth)acrylic acid to the copolymerizable monomer in the pressure-sensitive adhesive acryl-type copolymers is preferably in the range of 50-99/1-50 by weight, which results in a balance of aggregation properties and adhesivity to the skin.

Among the above hydrophobic polymers, preferred are polymers having a lower skin-stimulus and excellent solubility for the drugs, especially copolymers of (meth)acrylic acid alkyl esters, (meth)acrylic acid alkyl esters containing ether linkage in the molecule and the other copolymerizable monomers other set forth above. In this case, the proportion of the (meth)acrylic acid alkyl esters, the (meth)acrylic acid alkyl esters containing ether linkage in the molecule and the copolymerizable monomers other than these is in the range of 40-80/- 59-10/1-40.

In cases where the above hydrophobic polymers are likely to leave a paste on the applied site of the skin upon removal due to the shortage of aggregation strength, and cause soiling on the skin, it is preferable to subject the composition to an appropriate chemical crosslinking treatment (copolymerization of the monomers having crosslinking properties, further addition of a crosslinking agent, etc.) or physical crosslinking treatment (radiation of radioactive rays such as electronic rays causing electrolytic dissociation, crosslinking by ultraviolet rays, etc.) to a degree not impairing the adhesive properties.

In the present invention, the above-mentioned hydrophobic polymers have a glass transition temperature (Tg) ranging from $-65°$ C. to $35°$ C., preferably $-50°$ C. to $0°$ C.

The percutaneous absorption-promoting agents (ingredient ③) to be used in the present invention can be defined, in brief, as materials which promote release of the medicinal ingredients from the composition and/or migration of the medicinal ingredients into the body. Examples of these agents include a wide variety of substances improving solubility or dispersibility of the medicinal ingredients in the plaster layer, skin keratin emollient properties and permeation of drugs into skin keratin, auxiliaries for permeation of drugs into skin keratin, agents for dilation of pores of the skin, substances for changing the surface conditions and the like.

These percutaneous absorption-promoting agents are generally classified into hydrophobic absorption-promoting agents and hydrophilic absorption-promoting agents. Examples of the hydrophobic absorption-promoting agents include aliphatic carboxylic acids having 6-20 carbon atoms, preferably 10-20 carbon atoms, their lower alcohol esters, and aliphatic alcohols having 6-20 carbon atoms, preferably 10-20 carbon atoms.

As the aliphatic carboxylic acids having 6-20 carbon atoms, for example, saturated or unsaturated aliphatic monocarboxylic or dicarboxylic acids such as caproic acid, caprylic acid, lauric acid, myristic acid, palmitic acid, stearic acid, arachic acid, obtusilic acid, linderic acid, oleic acid, linoleic acid, linolenic acid, arachidonic acid may be used in the present invention and sebacic acid. As the lower alcohol esters of the aliphatic carboxylic acids having 6-20 carbon atoms, mention can be made of, for example, esters of lower alcohol having about 1-5 carbon atoms (e.g. methanol, ethanol, propanol, 2-propanol, butanol, pentanol) and the afore-mentioned aliphatic acids having 6-20 carbon atoms. As the lower alcohol esters of the aliphatic dicarboxylic acids, for example, mono- or diester in which one of the carboxyl groups or two of the carboxyl groups thereof is(are) esterified may be used. Specific examples of the lower alcohol esters of the aliphatic carboxylic acids having 6-20 carbon atoms include diesters of sebacinic acid, isopropyl esters of myristic acid, etc.

As the before-mentioned aliphatic alcohols having 6-20 carbon atoms, for example, saturated or unsaturated aliphatic alcohols such as caproyl alcohols, caprylyl alcohols, capryl alcohols, lauryl alcohols, myristyl alcohols, cetyl alcohols, stearyl alcohols, oleyl alcohols, linoleyl alcohols may be used and linolenyl alcohols.

Among the aliphatic carboxylic acids, lower alcohol esters of the aliphatic carboxylic acids and the aliphatic alcohols, preferred are lower ($C_{1-5}$) alcohol esters of the aliphatic monocarboxylic acids, most preferably isopropyl myristate.

As the hydrophilic absorption-promoting agents, mention can be made of, for example, alkanepolyols.

As the alkanepolyols, for example, lower alkanediols having 2-5 carbon atoms such as ethylene glycol (1,2-ethanol), propylene glycol (1,2-propanediol), 1,3-propanediol, 1,2-butanediol, 1,3-butanediol, 1,4-butanediol, 2,3-butanediol and 1,5-pentanediol, and lower alkanetriols having 2-5 carbon atoms of glycerine may be utilized. Among others, particularly preferred are propylene glycol and 1,3-butanediol.

Two or more species of the above-mentioned percutaneous absorption-promoting agents can be used in combination, and hydrophobic absorption-promoting agents and hydrophilic absorption-promoting agents may be used in combination.

While the amount of the absorption-promoting agents is optional, the preferred total amount is in the range from 0.1 to 80% by weight, more preferably from 1 to 50% by weight.

In the present invention, water (ingredient ④) is essentially incorporated as a solubilizer for the medicinal ingredients.

Water is especially selected as an ingredient for the adhesive compositions of the present invention owing to the following advantageous properties set forth below.

1) It is a bio-component.
2) It, as a solubilizer, gives a lower stimulus to the skin.
3) It is easy to adjust the pH of the plaster layer to be brought into contact with the skin to nearly neutral by addition of a small amount of inorganic substances.
4) It is less reactive to medicinal ingredients and thus able to retain medicinal ingredients stably in the preparation.
5) It eliminates individual differences in the water content of the skin, to enable the adhesives to exhibit pharmacological effects with little variation resulting from individual skin differences.

Examples of water-containing percutaneously absorbable preparations include ointments, creams, lotions, liquid preparations, suspensions and emulsions besides adhesives, which are classified into solution types and dispersion types exemplified by W/O types (water in oil) and O/W types (oil in water). In order to obtain an adhesive containing water, having a high shape-retention, and excellent in stability not only during storage but also during the period from administration to removal, which meets the objects of the invention, a hydrophobic polymer which is a continuous phase, namely, a W/O type, should be selected as a base.

The amount of water to be incorporated is not limited as long as it enables the plaster layer to be a W/O type. Not all the medicinal ingredients to be incorporated need be dissolved in water. That is, a part of the medicinal ingredients may remain solid in the plaster layer. The particularly preferred amount of water is in the range of from 1 to 20% by weight by water content of the plaster layer. If the water content of the plaster layer is less than 1% by weight, release of the medicinal ingredients from the preparation tends to be poor, leading to failure to exhibit expected medicinal effects. On the other hand, if the water content is over 20% by weight, containing and retaining the medicinal ingredients and percutaneous absorption-promoting agents as well as water stably in the plaster layer for long periods tends to be difficult.

In the present invention, a solubilizer may be incorporated as an ingredient of the plaster layer, so the medicinal ingredient is dissolved more completely in water. As the solubilizers, acidic or basic, inorganic or organic substances may be used. Examples of the inorganic acidic substances include hydrochloric acid, sulfuric acid, nitric acid and phosphoric acid. Examples of the organic acidic substances include acetic acid, lactic acid, maleic acid, citric acid, succinic acid and tartaric acid. Examples of the inorganic basic substances include sodium hydroxide, potassium hydroxide, sodium carbonate, potassium carbonate, sodium hydrogencarbonate and potassium hydrogencarbonate. Examples of the organic basic substances include amines such as triethanolamine, diethanolamine, triisopropanolamine, diisopropanolamine, etc., and amino acids such as L-arginine.

The solubilizers are added to dissolve the medicinal ingredients in an optional proportion in the plaster layer, and while the amount of the solubilizers to be added is dependent upon the amount of a drug to be incorporated, it is preferably in the range of 0.01 to 30% by weight, more preferably in the range of 0.1 to 20% by weight.

The hydrophilic polymer (ingredient ⑤) is a polymer which is soluble or capable of swelling in water, and it is incorporated to increase the viscosity of water and, in some cases, that of the hydrophilic percutaneous absorption-promoting agents, thereby retaining these ingredients stably in the plaster layer. Such hydrophilic polymers include, for example, water-soluble polymers and water-aborbing polymers.

As the water-soluble polymers, natural water-soluble polymers such as starch types, pullulan types, cellulose types, tannin types, lignin types, alginic acid, gum arabic, gum guar, gum tragacanth and gelatin, and synthetic polymers such as polyvinyl alcohol types, polyvinyl ethyleneoxide types, acrylic acid types, maleic anhydride types, phthalic acid types, acrylamide types, polyvinyl pyrrolidones, polyamines, polyelectrolytes, urea types and melamine types may be used in the present invention.

As the water-absorbing polymers, preferred are polymers capable of absorbing water in at least, preferably about 50-2,000 times amount their own weight. These compounds include, for example, vinyl acetate-acrylic acid ester copolymer suspensions, polyacrylic acid salt types, polyvinyl alcohol-maleic anhydride crosslinked copolymers, isobutylene-maleic acid crosslinked copolymers, polyacrylonitrile graft polymer suspensions and starch-acrylic acid graft polymers.

The amount of these hydrophilic polymers to be used in the present invention is not particularly limited as long as it does not surpass the amount of the hydrophobic polymer (ingredient ②), and is preferably in the range of about 0.1 to 15% by weight, more preferably about 0.2 to 5% by weight.

The percutaneous preparations of the present invention may incorporate nonionic surfactants to enable uniform mixing of the respective ingredients.

As the nonionic surfactants, esters of polyoxyethylene sorbitan fatty acid (e.g. polyoxyethylene sorbitan monooleate, polyoxyethylene sorbitan monostearate, polyoxyethylene sorbitan monopalmitate, polyoxyethylene sorbitan monolaurate, etc.), esters of polyoxyethylene sorbitol fatty acid (e.g. polyoxyethylene sorbitol monolaurate, etc.), esters of polyoxyethylene fatty acid (e.g. polyoxyethylene stearate, etc.), polyoxyethylene higher alcohol ethers (e.g. polyoxyethylene lauryl alcohol, polyoxyethylene oleyl alcohol, etc.), polyoxyethylene alkylaryl ethers (e.g. polyoxyethylene nonyl phenol, etc.), polyoxyethylene castor oil derivatives (e.g. polyoxyethylene hydrogenated castor oil derivatives such as HCO-50, HCO-60, etc.), polyoxyethylene lanolin alcohol derivatives and block polymer type nonionic surfactants (e.g. pluronic, L-62, L-64, F-68, etc.) may be used. While the amount of the nonionic surfactant to be incorporated can be optionally selected as a whole provided that HLB is maintained in the range of 5 to 20, it is preferably about 0.5-20% by weight, more preferably about 0.5-10% by weight, most preferably about 1-8% by weight.

The adhesives of the present inventin can be produced by known means except the process for drying the plaster layer. Drying of the plaster layer is preferably conducted so the water content of the plaster layer after drying amounts to 1-20% by weight, and therefore, the drying is conducted at a temperature lower than that in the conventional drying of the plaster layers, for a shorter time, for example, at 65°-75° C. for about 1-5 minutes.

The plaster layer may contain a trace amount of solvent from the solution of the adherent compositions.

In case where the plaster layer is likely to leave a paste on the applied site of the skin upon removal due to the shortage of aggregation strength caused by water, percutaneous absorption-promoting agents and a large amount of the other liquid components contained in the plaster layer induces plasticization of the hydrophobic polymers, and deposit soil on the skin, it is preferable to place a porous base layer in the plaster layer or in contact with the plaster layer.

While there is no particular limitation on the porous base layer as long as it does not interfere with free diffusion and migration throughout the plaster layer and release toward the surface of the skin of the medicinal ingredients, percutaneous absorption-promoting agents, water and the other ingredients, it is also possible to permit the porous base layer to control the above-mentioned phenomena.

Examples of the porous base layers include sheet bases such as non-woven fabrics, woven fabrics, Japanese paper, porous films, pierced films, or the like.

The thickness of the porous base layer is preferably less than that of the plaster layer when the porous base layer is placed in the plaster layer. A thick porous base layer may be used as long as release of the medicinal ingredients is not adversely affected.

Figure 3:
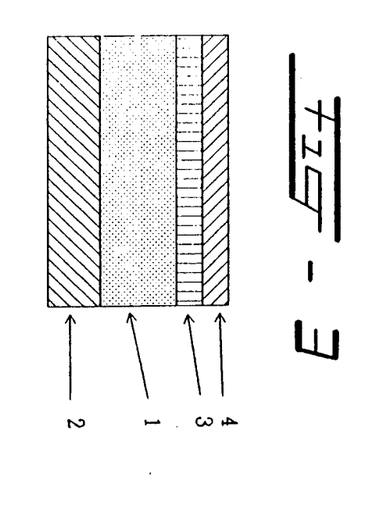
Figure 4:
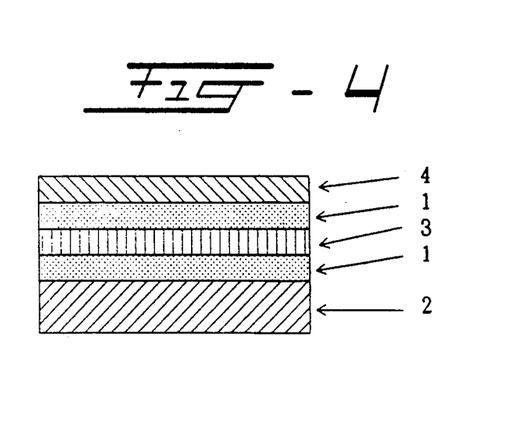

When a porous base layer placed in the plaster layer is thinner than the plaster layer, three different embodiments of preparation constitutions are generally contemplated depending on the positions of the porous base layer. That is, (I) an embodiment in which a porous base layer 3 is placed in contact with a backing layer 2 on the side toward the backing layer 2 of a plaster layer 1 (FIG. 2), (II) an embodiment in which the porous base layer 3 is placed in contact with the separate-type liner 4 on the side toward a separate-type liner 4 of the plaster layer 1 (FIG. 3) and (III) an embodiment in which the porous base layer 3 is placed out of contact with the backing layer 2 and the separate-type liner 4 in the plaster layer 1 (FIG. 4). In all of the above-mentioned embodiments, the plaster may be embedded in the porous base layer, whereby aggregation strength is enhanced with that of the plaster per se unchanged. In the above embodiments (II) and (III), the plasters are not necessarily required to be embedded in the porous base layers, and the ingredients of the plaster migrate through the porous base layer due to capillarity.

Figure 2:
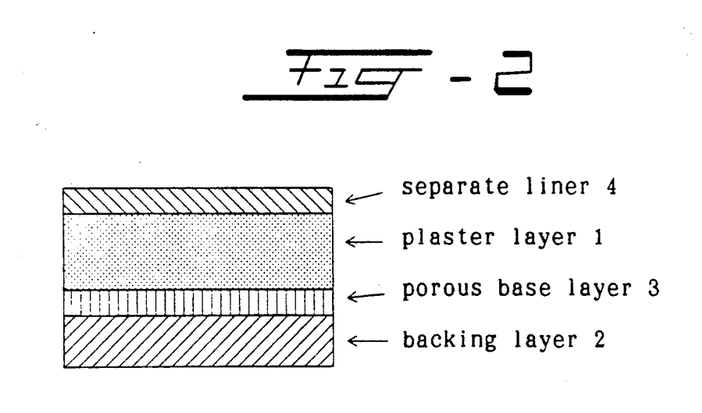
FIGS. 2-4 are cross sectional views of the adhesives of the present invention having a porous base layer, wherein 1 is a plaster layer, 2 is a backing layer, 3 is a porous base layer and 4 is a separate liner.

Among the embodiments (I), (II) and (III), the embodiment (I) is desirable in view of efficiency of production. The embodiment (1) offers an advantage in that the porous base layer can be laminated on the backing layer with a binder or the like.

The medical adhesives of the present invention solely can be applied to the skin alone or may be covered with other adhesives having a skin-adhering property, for example, surgical tapes, or with bandages after application of the adhesives for prevention of loosening.

Since the medical adhesive of the present invention comprises the plaster layer of the W/O type wherein the hydrophobic polymer which is the main constituent component of the continuous phase of the plaster and the hydrophilic polymer are incorporated in appropriate amounts, and the components have poor compatibility with the medicinal ingredients, percutaneous absorption-promoting agents, water and the other additives can be easily dissolved or dispersed homogeneously.

Accordingly, the medical adhesive has the effect that the medicinal ingredients and percutaneous absorption-promoting agents can be released stably, and thus, pharmacological effects can be sustained sufficiently over a long period.

Especially, a medical adhesive in which the water content of the plaster after formation is 1-20% by weight has the effect that the ingredients can be contained and retained in the formed preparations for a long period.

Below, the present invention is described in further detail by working examples, which are not limiting and can be modified in various ways. Hereinafter, "part" means "part by weight".

EXAMPLE 1

Fifteen parts of (R)-3-[(S)-1-carboxy-5-(4-piperidyl)-pentyl]amino-4-oxo-2,3,4,5-tetrahydro-1,5-benzothiazepine-5-acetic acid [hereinafter referred to as compound (I)], an angiotensin I transferase inhibitor, 20 parts of propylene glycol, 1.3 parts of sodium hydroxide, 30 parts of purified water and 1 part of crosslinked acrylic acid.vinyl alcohol copolymer were mixed for dissolution, to obtain a hydrophilic phase.

With twenty parts of isopropyl myristate and 5 parts of polyoxyethylen sorbitan monooleate was mixed for dissolution 38 parts (as the solid portion) of the copolymer solution (A) obtained by polymerizing a mixture of 55 parts of acrylic acid 2-ethylhexyl ester, 30 parts of acrylic acid methoxyethyl ester and 15 parts of vinyl acetate in ethyl acetate as the solvent by a conventional method to give a lipophilic phase.

The thus-obtained hydrophilic phase and lipophilic phase were uniformly mixed, applied onto a separate-type liner made of polyester of 75 μm in thickness so that the thickness of the plaster after drying became 100 μm, and dried at 70° C. for 4 minutes to form a plaster layer of a W/O type.

The plaster layer was adhered by rolling on the side of the polyethylene of a polyester film of 25 μm in thickness with the polyethylene of 30 μm in thickness laminated thereon and on the non-woven fabric side of a backing layer with the non-woven fabric sheet made of polyester laminated thereon at the basis weight of 40 g/m² to obtain a medical adhesive of the present invention.

EXAMPLE 2

In the same manner as in Example I except that 2 parts of the purified water was used in place of 30 parts thereof, an adhesive was obtained.

EXAMPLE 3

Fifteen parts of compound (I), 20 parts of lactic acid, 10 parts of purified water and 1 part of polyacrylic acid were mixed for dissolution to give a hydrophilic phase.

With a mixture of 20 parts of oleic acid and 50 parts of ethyl acetate was mixed for dissolution 34 parts (as the solid portion) of a methyl acrylate-2-ethylhexyl acrylate copolymer resin emulsion to give a lipophilic phase.

The thus-obtained hydrophilic phase and lipophilic phase were uniformly mixed, applied onto a polyester separate-type liner of 75 μm in thickness so that the thickness of the plaster after drying became 100 μm, and dried at 75° C. for 5 minutes to form a plaster layer of a W/O type.

After the plaster layer was adhered by rolling onto a backing layer made of a polyester film of 9 μm in thickness, the separate-type liner was stripped off and a nylon woven fabric was adhered by pressing onto the exposed plaster layer at the basis weight of 25 g/m², followed by adhesion of the separate-type liner to give a medical adhesive of the present invention.

EXAMPLE 4

Twelve parts of timolol maleate, 20 parts of propylene glycol, 1.5 parts of sodium carbonate, 30 parts of purified water, 2 parts of hydroxypropylcellulose and 5 parts of polyoxyethylene (15) oleyl ether were mixed for dissolution to give a hydrophilic phase.

With 25 parts of isopropyl myristate was mixed for dissolution 53 parts (as the solid portion) of a copolymer solution (B) obtained by conventional polymerization of 70 parts of acrylic acid 2-ethylhexyl ester and 30 parts of vinylpyrrolidone in ethyl acetate as the solvent to give a lipophilic phase.

The thus-obtained hydrophilic phase and lipophilic phase were uniformly mixed, applied onto a polyester separate-type liner of 75 μm in thickness so that the thickness of the plaster after drying became 50 μm, and dried at 68° C. for 4 minutes to form a plaster layer of a W/O type.

Two sheets of the plaster layer formed on the separate-type liner were prepared. After one of the plaster layers was adhered by rolling onto a backing layer made of a polyester film of 25 μm in thickness, the separate-type liner was stripped off. Japanese paper was laminated on the exposed surface of the other plaster layer at the basis weight of 20 g/m², whereon the exposed surface of the above-mentioned plaster layer adhered by rolling onto the backing layer was adhered by pressure to afford a medical adhesive of the present invention.

EXAMPLE 5

Ten parts of timolol maleate, 15 parts of 1,3-butandiol, 1.2 parts of potassium hydroxide, 40 parts of purified water and 1 part of polyacrylic acid were mixed for dissolution to give a hydrophilic phase.

With 20 parts of lauric acid, 4 parts of polyoxyethylene sorbitan monooleate and 3 parts of sorbitan monooleate were mixed for dissolution 46 parts (as the solid portion) of a copolymer solution (C) obtained by conventional polymerization of 93 parts of acrylic acid 2-ethylhexyl ester and 7 parts of acrylic acid in ethyl acetate as the solvent to give a lipophilic phase.

The thus-obtained hydrophilic phase and lipophilic phase were uniformly mixed, applied onto a polyester separate-type liner of 75 μm in thickness so that the thickness of the plaster after drying became 120 μm, and dried at 70° C. for 6 minutes to form a plaster layer of a W/O type.

The plaster layer was then adhered by rolling onto a backing layer of 6 μm in thickness made of a polyester film to afford a medical adhesive of the present invention.

EXAMPLE 6

Fifteen parts of diclofenac sodium, 20 parts of propylene glycol, 30 parts of purified water and 2 parts of carboxymethylcellulose sodium were mixed for dissolution to give a hydrophilic phase.

With 20 parts of isopropyl myristate and 5 parts of polyoxyethylene (60) hydrogenated castor oil was mixed for dissolution 38 parts (as the solid portion) of a copolymer solution (D) obtained by conventional polymerization of 70 parts of acrylic acid 2-ethylhexyl ester and 30 parts of vinyl acetate in ethyl acetate as the solvent to give a lipophilic phase.

The thus-obtained hydrophilic phase and lipophilic phase were uniformly mixed, applied onto the polyester separate-liner of 75 μm in thickness so that the thickness of the plaster after drying became 100 μm, and dried at 70° C. for 5 minutes to form a plaster layer of a W/O type.

The obtained plaster layer was then adhered by rolling onto a backing layer made of a polyester film of 25 μm in thickness to afford a medical adhesive of the present invention.

EXAMPLE 7

Twelve parts of diclofenac sodium, 25 parts of purified water and 2 parts of crosslinked acrylic acid-vinylalcohol copolymer were mixed for dissolution to give a hydrophilic phase.

With 20 parts of lauryl alcohol was mixed for dissolution 66 parts (as the solid portion) of a polymer solution (E) obtained by homogeneous mixing for dissolution of 25 parts of VISTANEX MML-80 (viscosity-average molecular weight 990,000) and 75 parts of HIMOL-4H (viscosity-average molecular weight 40,000) in n-hexane as the solvent to give a lipophilic phase.

The thus-obtained hydrophilic phase and lipophilic phase were uniformly mixed, applied onto a polyester separate-type liner of 75 μm in thickness so that the thickness of the plaster after drying became 100 μm, and dried at 75° C. for 5 minutes to form a plaster layer of a W/O type.

The plaster layer was then adhered by rolling onto a backing layer made of a polyester film of 25 μm in thickness to afford a medical adhesive of the present invention.

COMPARATIVE EXAMPLE 1

An attempt to obtain an adhesive in the same manner as in Example 1 except that the copolymer solution (A) was excluded from the ingredients to be incorporated resulted in failure.

COMPARATIVE EXAMPLE 2

An attempt to obtain an adhesive in the same manner as in Example 1 except that the copolymer solution (A) as the solid portion was incorporated in the proportion of 20 parts instead of 38 parts resulted in failure since the stable plaster layer could not be formed.

COMPARATIVE EXAMPLE 3

An adhesive was obtained in the same manner as in Example 1 except that the propylene glycol and isopropyl myristate as the percutaneous absorption-promoting agents were excluded from the ingredients to be incorporated.

COMPARATIVE EXAMPLE 4

An adhesive was obtained in the same manner as in Example 1 except that purified water was excluded from the ingredients to be incorporated.

COMPARATIVE EXAMPLE 5

An attempt to obtain an adhesive in the same manner as in Example 1 except that the crosslinked acrylic acid-vinyl alcohol copolymer as a hydrophilic polymer was excluded from the ingredients to be incorporated resulted in failure since an adhesive having a uniform and stable plaster layer could not be obtained due to separation between the hydrophilic phase and the lipophilic phase in the drying process at 70° C. for 4 minutes.

COMPARATIVE EXAMPLE 6

An adhesive was obtained in the same manner as in Example 3 except that oleic acid as a percutaneous absorption-promoting agent was excluded from the ingredients to be incorporated.

COMPARATIVE EXAMPLE 7

An adhesive was obtained in the same manner as in Example 3 except that the proportion of the purified water to be incorporated was changed from 10 parts to 70 parts, but the liquid ingredients blotted on the surface of the plaster layer immediately after preparation. Thus, the adhesive was considered to fail to retain the liquid ingredients stably and was not subjected to the animal tests as shown below.

COMPARATIVE EXAMPLE 8

An attempt to obtain an adhesive in the same manner as in Example 4 except that the copolymer solution (B) was excluded from the ingredients to be incorporated resulted in failure.

COMPARATIVE EXAMPLE 9

An adhesive was obtained in the same manner as in Example 5 except that the 1,3-butandiol as a percutaneous absorption-promoting agent, potassium hydroxide and purified water were excluded from the ingredients to be incorporated.

COMPARATIVE EXAMPLE 10

An attempt to obtained an adhesive in the same manner as in Example 6 except that the proportion of the copolymer solution (D) as the solid portion to be incorporated was changed from 38 parts to 25 parts resulted in failure since a stable layer containing medicinal ingredient could not be formed.

COMPARATIVE EXAMPLE 11

An attempt to obtain an adhesive in the same manner as in Example 7 except that the crosslinked acrylic acid.vinyl alcohol copolymer which is a hydrophilic polymer was excluded from the ingredients to be incorporated resulted in failure since an adhesive having a uniform plaster layer could not be obtained due to separation of the hydrophilic phase from the lipophilic phase in the drying process.

EXPERIMENTAL EXAMPLE

The water contents were quantitatively determined for the plaster layers of all Examples in which the uniform and stable plaster layers could be prepared, the plaster layers of Comparative Examples 3, 4, 6 and 9 and the unstable plaster layer obtained according to Comparative Example 7. As far as Comparative Example 7 was concerned, the plaster layer from which the blotted liquid ingredients were wiped off with filter paper was quantitatively determined for the water content. Furthermore, for the above-mentioned adhesives other than the adhesive according to Comparative Example 7, animal experiments were conducted.

EXPERIMENTAL EXAMPLE 1

Quantitative determination of the water content

Water was extracted from the pieces of the size of 5×5 cm (=25 cm²) cut out from the adhesives of Examples 1–7 and Comparative Examples 3, 4, 6, 7 and 9 with anhydrous methanol with sufficient care prohibiting entry of external moisture, and subjected to chromatography to quantitatively determine the water content in the adhesives.

The results of this test are shown in Table 1. In table, each of the indicated values is the mean value of three samples.

EXPERIMENTAL EXAMPLE 2

Test of adhesion to rabbits . . . migration property of medicinal ingredient into the skin The pieces of the size of 30 mmφ cut out from the adhesives of Examples 1–7 and Comparative Examples 3, 4, 6 and 9 were adhered to the skin in the depilated back of rabbits (male white Japanese native species aged 12 weeks) for 24 hours and stripped off. The residual medicinal ingredient was quantitatively determined by high performance liquid chromatography, and the apparent migration ratio of the midicinal ingredient to the skin based on the initial content (hereinafter referred to briefly as skin-migration ratio) was calculated.

The results of these tests are shown in Table 1. In Table, each of the indicated values is the mean value of three samples.

EXPERIMENTAL EXAMPLE 3

Test of adhesion to rats . . . change in concentration in blood of medicinal ingredient The round pieces cut out from the adhesives were adhered to the skin in the depilated abdomens of male SD rats aged 9 weeks at the dose of the medicinal ingredient of 6 mg/rat for compound (I), 10 mg/rat for timolol maleate and 10 mg/rat for diclofenac sodium for 24 hours. Blood was collected at 5, 7 and 24 hours' lapse after adhesion. The medicinal ingredient was extracted from the blood in accordance with a conventional method, and the concentration in blood was quantitatively determined by gas chromatography or high performance liquid chromatography.

Figure 1:
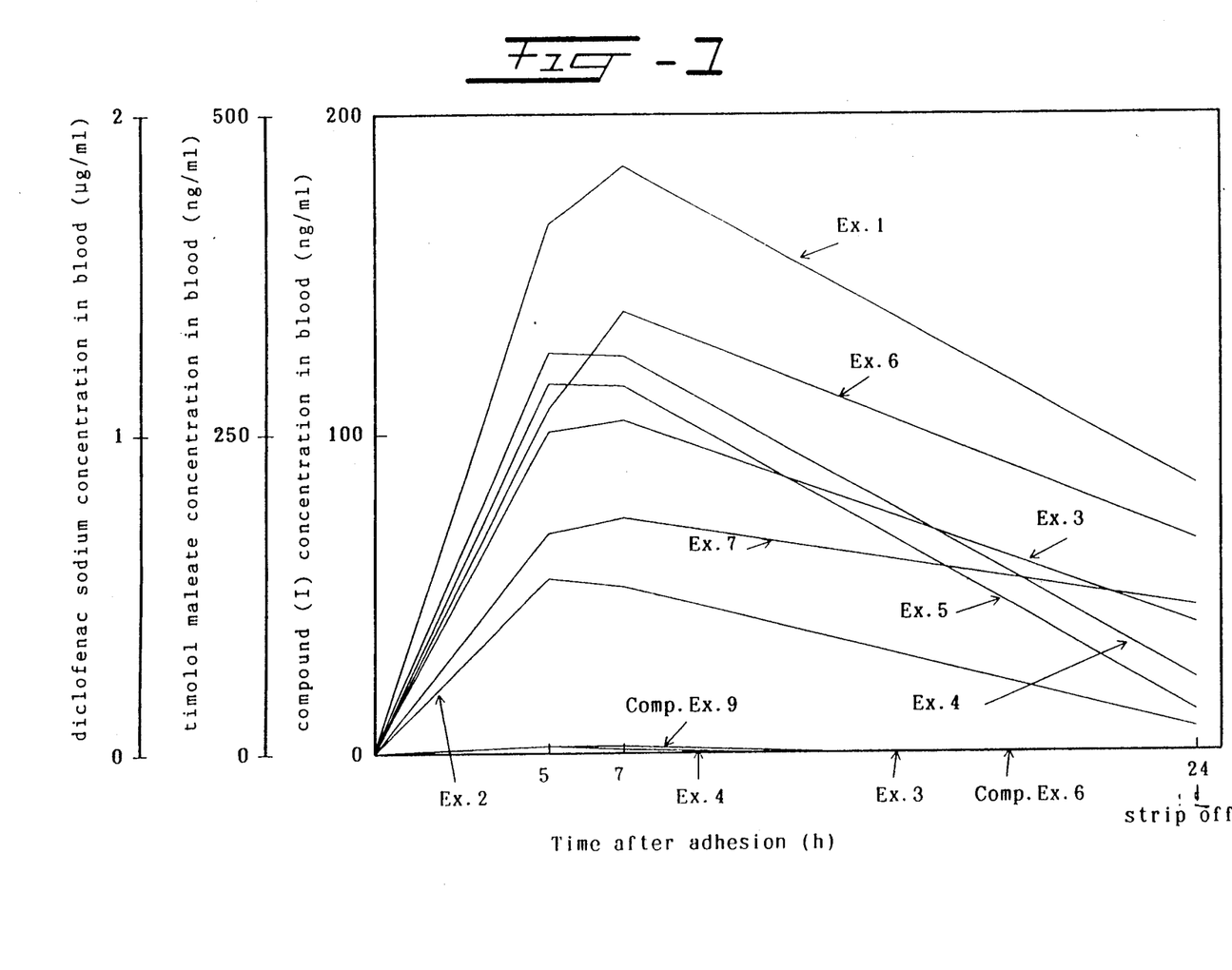
FIG. 1 is a graph showing the change in concentration in blood of the medicinal ingredient in each adhesive.

The test results are shown in FIG. 1. Each of the values indicates the mean value of three samples.

TABLE 1

|  | Medicinal ingredient | Water content (% by weight) | Skin-migration ratio (%) |
|---|---|---|---|
| Example |  |  |  |
| 1 | Compound (I) | 7.1 | 61.5 |
| 2 | Compound (I) | 0.7 | 26.5 |
| 3 | Compound (I) | 3.3 | 47.8 |
| 4 | Timolol maleate | 8.4 | 58.9 |
| 5 | Timolol maleate | 12.9 | 63.3 |
| 6 | Diclofenac sodium | 6.0 | 20.8 |
| 7 | Diclofenac sodium | 3.1 | 17.2 |
| Comparative Example |  |  |  |
| 3 | Compound (I) | 5.8 | 49.2 |
| 4 | Compound (I) | ≈0.0 | 15.3 |
| 6 | Compound (I) | 3.6 | 42.5 |
| 7 | Compound (I) | 21.7 | — |
| 9 | Timolol maleate | ≈0.0 | 2.1 |

What is claimed is:

1. A medical preparation comprising a plaster layer containing the following ingredients:
   (1) a medicinal ingredient in the range of 0.1 to 15% by weight;
   (2) a hydrophobic polymer in the range of 25 to 80% by weight, selected from the group consisting of acrylic polymers, silicone gums, polyisobutylene gums, polyisoprene gums, styrene-butadiene-styrene block copolymer gums, styrene-isoprene-styrene block copolymer gums, poly vinylalkyl ethers, poly vinyl-acetate, poly vinyl-propionate and polyurethane elastic bodies, said hydrophobic polymer having a glass transistion temperature (Tg) of −50° C. to 0° C.;
   (3) a percutaneous absorption-promoting agent in the range of 0.1 to 80% by weight;
   (4) water in the range of 0.1 to 20% by weight; and,
   (5) a water soluble or water-absorbing polymer in the range of 0.1 to 15% by weight;
   wherein said ingredient (2) constitutes a continuous phase of said plaster layer and said ingredients (4) and (5) are dispersed in said continuous phase of ingredient (2).

2. A medical preparation as claimed in claim 1 wherein the solubility of the medicinal ingredient is at least 1 g or 1 ml per 10,000 ml of water.

3. A medical preparation as claimed in claim 2, wherein the medicinal ingredient is selected from the group consisting of (R)-3-[(S)-1-carboxy-5-(4-piperidyl)pentyl]amino-4-oxo-2,3,4,5-tetrahydro-1,5-benzothiazepine-5-acetic acid, timolol maleate and diclofenac sodium.

4. A medical preparation as claimed in claim 1, wherein the hydrophobic polymer having a Tg of −50° C. to 0° C. is a pressure-sensitive acrylic adhesive polymer.

5. A medical preparation as claimed in claim 4, wherein the pressure-sensitive acrylic adhesive polymer comprises (meth)acrylic acid alkyl ester and a copolymerizable monomer in a mixing ratio of 50-99/1-50 by weight.

6. A medical preparation as claimed in claim 4, wherein the pressure-sensitive acrylic adhesive polymer is a copolymer of (meth)acrylic acid alkyl ester, (meth)acrylic acid alkyl ester containing an ether linkage and a copolymerizable monomer; the proportion of the (meth)acrylic acid alkyl ester, (meth)acrylic acid alkyl ester containing an ether linkage and a copolymerizable monomer being 40-80/59-10/1-40 by weight.

7. A medical preparation as claimed in claim 1, wherein the hydrophobic polymer having a Tg of 50° C. to 0° C. is crosslinked.

8. A medical preparation as claimed in claim 1, wherein the percutaneous absorption-promoting agent is at least one species selected from the group consisting of aliphatic carboxylic acids having 6-20 carbon atoms, their lower alcohol esters, aliphatic alcohols having 6-20 carbon atoms and alkanepolyols.

9. A medical preparation as claimed in claim 1, wherein the hydrophilic polymer soluble or capable of swelling in water is a water-absorbing polymer capable of absorbing 50-2,000 times amount its own weight of water.

10. A medical preparation as claimed in claim 1, which comprises a porous base layer in the plaster layer or in contact with the plaster layer.

11. A medical preparation as claimed in claim 1, wherein the porous base layer is placed in contact with a backing layer on the side toward the backing layer of the plaster layer.

12. A medical preparation as claimed in claim 1, wherein the water soluble polymer is selected from the group consisting of starch, pullulan, cellulose, tannin, lignin, alginic acid, gum arabic, gum guar, gum tragacanth, gelatin, polyvinyl alcohol, polyvinyl ethyleneoxide, acrylic acid, maleic anhydride, phthalic acid, acrylamide, polyvinyl pyrrolidones, polyamines, polyelectrolytes, urea and melamine.

13. A medical preparation as claimed in claim 1, wherein the water-absorbing polymer is selected from the group consisting of vinyl acetate-acrylic acid ester copolymer suspensions, polyacrylic acid salts, polyvinyl alcohol-maleic anhydride crosslinked copolymers, isobutylene-maleic acid crosslinked copolymers, polyacrylonitrile graft polymer suspensions and starch-acrylic acid graft polymers.

14. A medical preparation comprising a plaster layer containing the following ingredients:
(1) a medicinal ingredient in the range of 0.1 to 15% by weight;
(2) a hydrophobic polymer in the range of 25 to 80% by weight, selected from the group consisting of acrylic polymers, silicone gums, polyisobutylene gums, polyisoprene gums, styrene-butadiene-styrene block copolymer gums, styrene-isoprene-styrene block copolymer gums, poly vinylalkyl ethers, poly vinyl-acetate, poly vinyl-propionate and polyurethane elastic bodies;
(3) a percutaneous absorption-promoting agent in the range of 0.1 to 80% by weight;
(4) water in the range of 0.1 to 20% by weight; and,
(5) a water soluble or water-absorbing polymer in the range of 0.1 to 15% by weight;
wherein said ingredient (2) constitutes a continuous phase of said plaster layer and said ingredients (4) and (5) are dispersed in said continuous phase of ingredient (2).

* * * * *

UNITED STATES PATENT AND TRADEMARK OFFICE
CERTIFICATE OF CORRECTION

PATENT NO. : 5,176,916
DATED : January 5, 1993
INVENTOR(S) : Akihito Yamanaka et al It is certified that error appears in the above-indentified patent and that said Letters Patent is hereby corrected as shown below:

On the title page, item [73] Assignee: Delete "NITTO ELECTRIC INDUSTRIAL CO., LTD." and insert --NITTO DENKO CORPORATION--.

Signed and Sealed this

Twentieth Day of June, 1995

*Attest:*

BRUCE LEHMAN

*Attesting Officer*    *Commissioner of Patents and Trademarks*